United States Patent [19]

Kitson et al.

[11] Patent Number: 4,990,655

[45] Date of Patent: Feb. 5, 1991

[54] ALCOHOLS PRODUCTION BY HYDROGENATION OF CARBOXYLIC ACIDS

[75] Inventors: Melanie Kitson, Staines; Peter S. Williams, Hull, both of England

[73] Assignee: BP Chemicals Limited, London, England

[21] Appl. No.: 282,053

[22] Filed: Dec. 9, 1988

Related U.S. Application Data

[60] Division of Ser. No. 150,453, Jan. 29, 1988, Pat. No. 4,804,791, which is a continuation of Ser. No. 65,677, Jun. 18, 1987, abandoned, which is a continuation of Ser. No. 849,050, Apr. 7, 1986, abandoned.

[30] Foreign Application Priority Data

Apr. 13, 1985 [GB] United Kingdom ............... 8509530

[51] Int. Cl.$^5$ .................... C07C 67/00; C07C 69/003
[52] U.S. Cl. ....................................................... 500/265
[58] Field of Search ........................................ 560/265

[56] References Cited

U.S. PATENT DOCUMENTS

| | | | |
|---|---|---|---|
| 1,839,974 | 1/1932 | Lazier | 560/265 |
| 4,104,478 | 8/1978 | Trivedi | 568/885 |
| 4,338,221 | 7/1982 | Qualeitti | 568/885 |
| 4,340,546 | 7/1982 | Qualeitti et al. | 260/410.9 N |
| 4,398,039 | 8/1983 | Pesa et al. | 560/265 |
| 4,443,639 | 4/1984 | Pesa et al. | 568/885 |
| 4,724,100 | 2/1988 | Gilbert et al. | 560/265 |

FOREIGN PATENT DOCUMENTS

| | | |
|---|---|---|
| 0192587 | 8/1986 | European Pat. Off. ............ 560/265 |
| 2340922 | 9/1977 | France . |
| 2505819 | 11/1982 | France . |
| 1534232 | 11/1978 | United Kingdom . |

*Primary Examiner*—J. E. Evans
*Attorney, Agent, or Firm*—Brooks Haidt Haffner & Delahunty

[57] ABSTRACT

Ethanol is produced from acetic acid or propanol is produced from propionic acid by contacting either acetic acid or propionic acid in the vapor phase with hydrogen at elevated temperature and a pressure in the range from 1 to 150 bar in the presence of a catalyst comprising as essential components (i) a noble metal of Group VIII of the Periodic Table of the Elements, and (ii) rhenium, optionally on a support, for example a high surface area graphitized carbon.

10 Claims, No Drawings

ALCOHOLS PRODUCTION BY HYDROGENATION OF CARBOXYLIC ACIDS

This application is a division of 150,453 Jan. 29, 1988 now U.S. Pat. No. 4,804,791, which in turn is a continuation of 065,677 Jun. 18, 1987, now abandoned which in turn is a continuation of 849,050, Apr. 7, 1986, now abandoned.

The prevent invention relates in general to the hydrogenation of carboxylic acids. In particular the present invention relates to a process for the hydrogenation of acetic and propionic acids in the presence of a catalyst comprising a noble metal of Group VIII of the Periodic Table of the Elements and rhenium to produce respectively ethanol and propanol.

The hydrogenation of carboxylic acids to produce the corresponding alcohol using supported Group VIII noble metal catalysts is known from, for example, U.S. Pat. Nos. 4,524,225; 4,104,478; GB-A-Nos. 1534232; 1551741 and EP-A-No. 147219. Of the aforesaid patents, all except GB-A-No. 1534232 relate to the hydrogenation of $C_4$ and higher carboxylic acids and, in common with GB-A-No. 1534232, to operation in the liquid phase. Moreover, EP-A-No. 147219 represents an intervening publication in the sense that it was published after the priority date claimed for the subject application on an application claiming an earlier priority date than the subject application.

GB-A No. 1534232 relates to the production of alcohols by the catalytic hydrogenation of carboxylic acids, including acetic acid and propionic acid, at elevated temperature and pressure in the presence of water and/or solvents using as catalyst palladium/rhenium on a support, the palladium to rhenium weight ratio of the catalyst being in the range from 0.01 to 5:1. The process is operated at pressures in the range from 50 to 1000 atmospheres. The only processes exemplified are the hydrogenation of $C_4$ and higher dibasic acids at very high pressures.

We have found that operation of a Group VIII noble metal catalyst in the liquid phase suffers from the disadvantage that leaching of both rhenium and Group VIII noble metal from the catalyst can occur. Not only leaching of the catalytic metals but also undesirable leaching of oxide-containing supports can occur. We have now suprisingly found that operation in the vapour phase provides high and comparatively long-lived catalytic activity and selectivity at lower pressures than those previously employed. Furthermore, operation in the vapour phase substantially overcomes the leaching problem associated with liquid phase operation.

Accordingly, the present invention provides a process for the production of either ethanol from acetic acid or propanol from propionic acid which process comprises contacting either acetic acid or propionic acid in the vapour phase with hydrogen at elevated temperature and a pressure in the range from 1 to 150 bar in the presence of a catalyst comprising an essential components (i) a noble metal of Group VIII of the Periodic Table of the Elements, and (ii) rhenium.

In addition to the alcohol, the process of the invention generally produces the corresponding ester as a by-product, for example the hydrogenation of acetic acid generally also produces ethyl acetate and the hydrogenation of propionic acid generally also produces propyl propionate. The proportion of the ester in the product may be increased, if desired, by for example operating at low conversions, for example at less than 50% conversion per pass, or by introducing an acidic function into the catalyst to promote 'in situ' esterification. Alternatively, the proportion of alcohol may be increased, for example by co-feeding water or by operating at very high conversions per pass.

Both acetic and propionic acids are commercially available in large tonnages and may be used in the process of the present invention in their commercially available forms without further purification. Alternatively, they may be further purified if desired.

Hydrogen, too, is commercially available on a large scale and may be used with or without further purification.

The catalyst comprises a first component which is a noble metal of Group VIII and a second component which is rhenium. For the avoidance of doubt, the noble metals of Group VIII are the metals osmium, palladium, platinum, rhodium, ruthenium and iridium. Of the aforesaid metals of Group VIII, palladium and ruthenium are preferred.

Preferably the catalyst further includes a support. Suitable supports include high surface area graphitised carbons, graphites, silicas, aluminas and silica/aluminas, of which high surface area graphitised carbons and silicas are preferred. Preferred silica supports are those having a high surface area, typically greater than 50 $m^2/g$.

Particularly preferred supports are the high surface area graphitised carbons described in GB-A No. 2136704 (BP Case No. 5536). The carbon is preferably in particulate form e.g. as pellets. The size of the carbon particles will depend on the pressure drop acceptable in any given reactor (which gives a minimum pellet size) and reactant diffusion constraint within the pellet (which gives a maximum pellet size). The preferred minimum pellet size is 0.5 mm and the preferred maximum is 10 mm, e.g. not more than 5 mm.

The carbons are preferably porous carbons. With the preferred particle sizes the carbon will need to be porous to meet the preferred surface area characteristics.

Carbons may be characterized by their BET, basal plane, and edge surface areas. The BET surface area is the surface area determined by nitrogen adsorption using the method of Brunauer Emmett and Teller J. Am. Chem. Soc. 60,309 (1938). The basal plane surface area is the surface area determined from the heat of adsorption on the carbon of n-dotriacontane from n-heptane by the method described by Proc. Roy. Soc. A314 ages 473–498, with particular reference to page 489. The edge surface area is the surface area determined from the heat of adsorption on the carbon of n-butanol from n-heptane as described in the Proc. Roy. Soc. article mentioned above with particular reference to page 495.

The preferred carbons for use in the present invention have a BET surface area of at least 100 $m^2/g$, more preferably at least 200 $m^2/g$, most preferably at least 300 $m^2/g$. The BET surface area is preferably not greater than 1000 $m^2/g$, more preferably not greater than 750 $m^2/g$.

The ratio of BET to basal plane surface area is preferably not greater than 4:1, more preferably not greater than 2.5:1. It is particularly preferred to use carbons with ratios of BET to basal plane surface area of not greater than 1.5:1.

It is preferred to use carbons with ratios of basal plane surface area to edge surface area of at least 10:1, preferably at least 100:1. It is not believed that there is an upper limit on the ratio, although in practice it will not usually exceed 200:1.

The preferred carbon support may be prepared by heat treating a carbon-containing starting material. The starting material may be an oleophillic graphite e.g. prepared as disclosed in GB No. 1,168,785 or may be a carbon black.

However, oleophillic graphites contain carbon in the form of very fine particles in flake form and are therefore not very suitable materials for use as catalyst supports. We prefer to avoid their use. Similar considerations apply to carbon blacks which also have a very fine particle size.

The preferred materials are activated carbons derived from vegetable materials e.g. coconut charcoal, or from peat or coal or from carbonizable polymers. The materials subjected to the heat treatment preferably have particle sizes not less than these indicated above as being preferred for the carbon support.

The preferred starting materials have the following characteristics: BET surface area of at least 100, more preferably at least 500 m$^2$/g.

The preferred heat treatment procedure for preparing carbon supports having the defined characteristics, comprise successively (1) heating the carbon in an inert atmosphere at a temperature of from 900° C. to 3300° C., (2) oxidizing the carbon at a temperature between 300° C. and 1200° C., (3) heating in an inert atmosphere at a temperature of between 900° C. and 3000° C.

The oxidation step is preferably carried out at temperatures between 300° and 600° C. when oxygen (e.g. as air) is used as the oxidising agent.

The duration of the heating in inert gas is not critical. The time needed to heat the carbon to the required maximum temperature is sufficient to produce the required changes in the carbon.

The oxidation step must clearly not be carried out under conditions such that the carbon combusts completely. It is preferably carried out using a gaseous oxidizing agent fed at a controlled rate to avoid over oxidation. Examples of gaseous oxidising agents are steam, carbon dioxide, and gases containing molecular oxygen e.g. air. The oxidation is preferably carried out to give a carbon weight loss of at least 10% wt based on weight of carbon subjected to the oxidation step, more preferably at least 15% wt.

The weight loss is preferably not greater than 40% wt of the carbon subjected to the oxidation step, more preferably not greater than 25% wt of the carbon.

The rate of supply of oxidizing agent is preferably such that the desired weight loss takes place over at least 2 hours, more preferably at least 4 hours.

When an inert atmosphere is required it may be supplied by nitrogen or an inert gas.

Suitably the catalyst comprises from 0.1 to 10% by weight Group VIII noble metal preferably from 0.5 to 5% by weight Group VIII noble metal and from 0.1 to 20% by weight rhenium, preferably from 1 to 10% by weight rhenium, the remainder of the catalyst comprising the support.

The catalyst may be further modified by the incorporation of a metal or metals of Group IA, Group IIA or Group IVA, preferably by a metal of Group IA of the Periodic Table of the Elements. A suitable metal is potassium. The amount of the modifying metal(s) may suitably be in the range from 0.1 to 20% by weight based on the total weight of the catalyst. The addition of a modifying metal to the catalyst can have the advantageous effect that carbon-carbon bond hydrogenolysis can be supressed to a greater or lesser extent during the hydrogenation, thereby improving the selectivity of the process to desired products.

The catalyst may be prepared by a variety of methods. One method of preparing the catalyst comprises impregnating the support with an aqueous solution of soluble compounds of rhenium and the Group VIII noble metal which compounds are thermally decomposable/reducible to the metal and/or metal oxide.

Impregnation may be by way of co-impregnation or sequential impregnation, preferably by sequential impregnation. Sequential impregnation is preferably effected in the order Group VIII noble metal followed by rhenium.

A preferred method of producing a catalyst for use in the process of the present invention comprises the steps of:

(A) impregnating a support with a solution of a soluble Group VIII noble metal compound thermally decomposable/reducible to Group VIII noble metal and subsequently removing the solvent therefrom, and (B) impregnating the Group VIII metal impregnated support with a solution in a solvent in which the Group VIII metal is substantially insoluble of a soluble rhenium compound thermally decomposable/reducible to rhenium metal and/or an oxide and thereafter removing the solvent therefrom.

Water may suitably be employed as the solvent in step (A) and a lower alkanol, for example ethanol, may be used as the solvent in step (B). The production of a catalyst in the aforesaid manner can avoid the palladium impregnated on the support in step (A) being leached to any appreciable extent in step (B) of the process.

Another preferred method of producing a catalyst for use in the process of the present invention comprises the steps of:

(A') impregnating a support with a solution of a soluble Group VIII noble metal compound thermally decomposable/reducible to the Group VIII noble metal and subsequently removing the solvent therefrom, (B') heating the Group VIII noble metal on the support, and (C') impregnating the Group VIII noble metal is impregnated support with a solution of a soluble rhenium compound thermally decomposable/reducible to rhenium metal and/or oxide and thereafter removing the solvent therefrom.

The Group VIII noble metal on the support may suitably be heated in the presence of either an inert gas, for example nitrogen, a reducing gas, for example hydrogen, or an oxygen-containing gas, for example air. Heating in the presence of an inert gas may suitably be accomplished at an elevated temperature in the range from 150° to 350° C. Heating in the presence of a reducing gas may suitably be accomplished at an elevated temperature in the range from 100° to 350° C. Heating in the presence of an oxygen-containing gas may suitably be accomplished at an elevated temperature in the range from 100° to 300° C., provided that when a high surface area graphitised carbon is used as support the upper temperature limit is 200° C.

In this embodiment of the invention it is not necessary that a solvent in which the Group VIII metal is substantially insoluble be used in step (C') of the process. Thus any suitable solvent may be used in steps (A') and (C') of the process. Suitable solvents include independently water and alkanols.

An advantage of the heating step (step (B')) is that the noble metal of Group VIII is rendered less prone to leaching in step (C') of the process.

Preferably, a further step is interposed either between step (A) and step (B) or between step (A') and step (B') wherein the Group VIII noble metal impregnated support is dried, suitably by heating at a temperature in the range from 50° to 150° C. It will be appreciated by those skilled in the art that this step may be incorporated into step (B'), if desired.

Suitable Group VIII noble metals which are decomposable/reducible to the metal include salts of the metals, for example carboxylates, nitrates and compounds in which the Group VIII noble metal is present in the anion moiety, for example ammonium tetrachloropalladate and ammonium tetranitropalladate. Suitable rhenium compounds which are decomposable/reducible to rhenium metal and/or oxide include dirhenium decacarbonyl, ammonium perrhenate and rhenium heptoxide.

The metal of Group IA, Group IIA or Group IVA of the Periodic Table of the elements may be added to the catalyst composition at any point during its preparation. Thus, the supported palladium/rhenium catalyst may be impregnated with a solution of a soluble compound of the metal. Alternatively, a soluble compound of the metal may be added to the co-impregnation solution or either of the sequential impregnation solutions.

A preferred catalyst comprises palladium and rhenium supported on a high surface area graphitised carbon of the type described in the aforesaid GB-A-No. 2136704. Contrary to the teaching of the aforesaid EP-A-No. 0147219 (cf Comparison C) regarding unacceptable selectivity losses and undesirable productivity losses in the hydrogenation of maleic acid when the average palladium crystallite size is 100 Angstroms or less, we have found that in the hydrogenation of acetic or propionic acids the catalyst selectivity and productivity is substantially independent of average palladium crystallite size in the range from 30 to 150 Angstroms. We may therefore use catalysts in which the average palladium crystallite size is in the range from 30 to 99.9 Angstroms.

Before use in the process of the invention the catalyst is preferably activated by contact at elevated temperature with either hydrogen or a hydrogen/inert gas, for example nitrogen, mixture for a period of from 1 to 20 hours. The elevated temperature may suitably be in the range from 200° to 350° C. Alternatively, the catalyst may be activated by heating to the reaction temperature in the presence of the reactants.

Whilst the precise nature of the catalyst on the support can not be determined with any degree of confidence, it is believed that the Group VIII noble metal component is in the form of the elemental metal and the rhenium component is in the form of the elemental metal and/or an oxide thereof.

The process of the invention may suitably be operated at an elevated temperature in the range from 100° to 350° C., preferably from 150° to 300° C. The pressure may suitably be less than 50 bar.

The process may be operated batchwise or continuously, preferably continuously. The catalyst may be employed in the form of a fixed bed, a moving bed or a fluidised bed. The Gas Hourly Space Velocity for continuous operation may suitably be in the range from 50 to 50,000 $h^{-1}$, preferably from 2000 to 30,000 $h^{-1}$.

The process of the invention will now be further illustrated by reference to the following Examples.

CATALYST PREPARATION

Catalysts were prepared according to the procedures outlined below. In the procedures, HSAG carbon denotes high surface area graphitised carbon, prepared and characterised as follows:

The carbon used as support was prepared from a commercially available activated carbon sold by Degussa under the designation BK IV. The activated carbon was heat treated as follows. The carbon was heated from room temperature in a stream of argon to 1700° C. over a period of about one hour. When the temperature reached 1700° C. the carbon was allowed to cool in the stream of argon to 25° C. The carbon was then heated in air in a muffle furnace at approximately 520° C. for a time known from experience to give a weight loss of 20% wt. The carbon was then heated in argon to between 1800° C. and 1850° C. in argon. The carbon was allowed to cool to room temperature in an argon atmosphere. The resulting graphite-containing carbon was then ground to 16-30 mesh BSS.

The resulting carbon had the following properties:

| | |
|---|---|
| BET surface area | 710 $m^2/g$ |
| basal plane surface area | 389 $m^2/g$ |
| edge surface area | 2.3 $m^2/g$ |
| BET/basal surface area ratio | 1.83 |
| basal plane/edge surface area ratio | 169 |

EXAMPLE 1

In the following procedures nominal loading is defined as weight of metal (not salt) added to the support expressed as a percentage of the weight of support.

A. An aqueous solution containing dissolved palladium nitrate and rhenium heptoxide ($Re_2O_7$) was added to HSAG carbon. The water was removed on a rotary evaporator, and the resulting impregnated carbon was then dried at 100° C. in a vacuum oven overnight. The amounts of the various components were chosen to give four catalysts with nominal loadings as follows: A1-2.5% Pd, 5% Re; A2-2.5% Pd, 2% Re; A3-2.5% Pd, 10% Re; A4-5% Pd, Re excluded from the preparation.

B. The procedure used in the preparation of catalyst A was followed, except that an appropriate amount of ammonium perrhenate was used instead of $Re_2O_7$, and the amounts of components were chosen to give four catalysts with nominal loadings as follows:
B1-5% Re, 2.5% Pd; B2-5% Re, 10% Pd; B3-5% Re, 0.5% Pd; B4-5% Re, Pd excluded.

C. An aqueous solution of palladium nitrate was added to HSAG carbon, the solvent was removed on a rotary evaporator, and the resulting impregnated carbon catalyst dried overnight at 100° C. in a vacuum oven. The catalyst was then cooled and transferred to a glass tube, and was then heated in a stream of hydrogen from ca 30° to 280° C. over a period of six hours. After ten hours at 280° C., the catalyst was cooled under hydrogen, and then purged for several hours with nitrogen.

The palladium on carbon was then mixed with an aqueous solution of $Re_2O_7$, the solvent again removed on a rotary evaporator, and the catalyst dried overnight at 100° C. in a vacuum oven. The amounts of palladium nitrate and rhenium heptoxide were chosen to give nominal loadings of 2.5% Pd and 5% Re in the final catalyst.

D. The procedure used in the preparation of catalyst C was repeated, except that prior to impregnation of rhenium, the palladium impregnated carbon catalyst was treated in nitrogen at 300° C. instead of hydrogen at 280° C.

E. The procedure used in the preparation of catalyst C was repeated, except that the hydrogen treatment step prior to impregnation of rhenium was replaced by an air treatment step as follows. The palladium impregnated carbon was heated from 20° to 180° C. in flowing air over six hours, and held at 180° C. for four hours, before cooling in air to 30° C.

F. This catalyst was prepared according to procedure C except that after drying, the palladium on carbon catalyst was not heated in hydrogen, and the solvent used for the impregnation of rhenium was ethanol instead of water.

G. Procedure C was used, except that immediately before the rhenium impregnation stage, the reduced palladium on carbon catalyst was treated in flowing nitrogen by heating from 30° C. to ca 650°–700° C. over three hours, holding at 650°–700° C. for a further sixteen hours, and then cooling to 30° C. The effect of this additional step was to increase the palladium crystallite size (as measured by XRD) from 30 Angstrom (catalyst from procedure C) to 150 Angstrom (catalyst from this procedure).

H. Catalysts containing ruthenium, rhenium and potassium were prepared as follows. HSAG carbon was mixed with a solution containing ruthenium trichloride and ammonium perrhenate, the solvent was removed on a rotary evaporator, and the resulting catalysts dried ca 100° C. overnight in a vacuum oven. The catalyst was then heated in flowing hydrogen from ca 30° to 300° C. over two hours, held at 300° C. for one hour, then cooled under hydrogen and purged with nitrogen. The reduced catalysts were then impregnated with potassium from an aqueous solution of potassium acetate. The amounts of the various ingredients were adjusted to give four catalysts with nominal loadings as follows:

H1–5% Re, 5% Ru, (K excluded); H2–5% Re, 5% Ru, 10% K; H3–5% Ru, 5% K (Re excluded); H4–5% Ru (Re and K excluded).

I. A catalyst containing ruthenium and rhenium was prepared according to procedure C, except that ruthenium nitrosyl nitrate replaced palladium nitrate, the ruthenium on carbon catalyst was dried at 120° C. not 100° C., and was then heated in hydrogen to 300° C. at 4° C./minute, and held at 300° C. for one hour. The amounts of the ingredients were chosen to give nominal loadings of 1% ruthenium and 10% rhenium.

J. A ruthenium/rhenium catalyst was prepared as in procedure I, except that rhenium was impregnated first.

K. Procedure A was used except that HSAG carbon was replaced by Davison 57 silica, ammonium tetrachloropalladate was used instead of palladium nitrate, and only one catalyst containing nominally 2.5% Pd and 5% Re was prepared.

L. Procedure C was used for the preparation of a catalyst containing platinum and rhenium. Tetrammine platinous hydroxide replaced palladium nitrate, and the nominal loadings were 1% Pt and 5% Re.

CATALYST TESTING

For experiments as pressures in the range 1–11 barg, 2.5 mls of catalyst was loaded into a corrosion resistant stainless steel tube of internal diameter 6–7 mm, and the reactor tube assembly placed in a tubular furnace. The catalyst was then activated by heating at atmospheric pressure in a stream of hydrogen to either 280° or 300° C. over a two hour period, and then holding at the final temperature for one hour. After activation, the catalyst was cooled in hydrogen to the desired reaction temperature. A mixture of carboxylic acid vapour and hydrogen was then passed over the catalyst, and pressure was adjusted to the required value by means of a back-pressure regulator. The vapour/hydrogen mixture was formed in a vapourising zone, to which acetic acid liquid and hydrogen gas were separately metered. The product vapours and gases leaving the reactor were sampled on-line and analysed by gas-liquid chromatography (glc).

For experiments conducted at 11–50 barg, a similar procedure and apparatus was used, except that the tube had internal diameter 10 mm, up to 10 mls of catalyst was employed, and products were passed to a condenser, and gas and liquid products were analysed separately, again by glc.

In both procedures, temperature was measured by means of a thermocouple inserted into the catalyst bed.

The product mixtures typically contained the appropriate alcohol and ester (the latter formed by esterification of alcohol with unreacted acid), together with traces of the appropriate dialkyl ether, and aldehyde, and by-product methane, ethane and (with propionic acid only) propane. In general, with carbon and silica supported catalysts, the main product is alcohol, especially at high conversions.

For the purposes of the Examples, conversions and selectivities have been calculated as respectively, the proportion of carboxylic acid hydrogenated, and the proportion of the hydrogenated carboxylic acid which is not converted into alkane by-product. Thus, selectivity denotes the ability of the catalyst to carry out hydrogenation without alkanation. In all examples (unless stated otherwise) only trace amounts ($\leq 2\%$) of dialkyl ether and aldehyde are formed.

DEFINITIONS

WHSV = Weight Hourly Space Velocity = kg liquid feed per kg catalyst per hour.

LHSV = Liquid Hourly Space Velocity = liters liquid feed per liter of catalyst per hour.

Productivity = kg acid converted per kg catalyst per hour.

EXAMPLES 2–7

Acetic acid was hydrogenated over the catalysts prepared in procedure A Example 1, and procedure C Example 1. The WHSV was ca 1.1 (LHSV = 0.35), the ratio hydrogen to acetic acid was ca 11:1 molar, and the pressure was 10.3 barg. In each case the catalyst was activated at 300° C., except for the catalyst of Example 7 (C), which was activated at 280° C. The results are collected in Table 1. Steady catalyst activity was observed in all cases. No deactivation was observed over run periods of up to 24 hours.

TABLE 1

| Example | Catalyst | T/°C. | Conversion (%) | Selectivity (%) |
|---|---|---|---|---|
| 2 | A1 | 222 | 27.2 | 91 |
| 3 | A1 | 202 | 15.0 | 90 |
| 4 | A2 | 202 | 6.3 | 93.6 |
| 5 | A3 | 201 | 38.2 | 95.9 |
| 6 | A4 | 200 | 0.6 | 30.4 |
| 7 | C | 217 | 52.1 | 93 |

The results show the benefit of sequential impregnation of Pd and Re (Example 7), and the poor performance of catalyst A4 (Example 6), which contains only palladium, and is not a catalyst according to the invention.

EXAMPLES 8-13

The same procedure as in Examples 2-7 was followed, but using the catalysts prepared according to procedure B Example 1. All catalysts were activated at 300° C. Results are presented in Table 2.

TABLE 2

| Example | Catalyst | T/°C. | Conversion (%) | Selectivity (%) |
|---|---|---|---|---|
| 8 | B1 | 180 | 15.4 | 97.0 |
| 9 | B1 | 210 | 37.5 | 95.1 |
| 10 | B1 | 239 | 69.0 | 89.0 |
| 11 | B2 | 210 | 45.0 | 95.0 |
| 12 | B3 | 210 | 18.5 | 96.9 |
| 13 | B4 | 210 | 13.7 | 97.6 |

The catalyst of Example 13 is not according to the present invention, and is included for the purposes of comparison.

EXAMPLES 14-17

The catalyst prepared by procedures C, D, E and F of Example 1 were compared in the hydrogenation of acetic acid. The procedure of Examples 2-7 was followed, except that the WHSV was ca 4 (LHSV=1.34), and the ratio hydrogen to acetic acid was 9:1 molar. The catalysts were activated at 280° C. before use, and the reaction temperature was 228°-230° C. Results are collected in Table 3.

TABLE 3

| Example | Catalyst | Productivity (kg/kg cat/h) | Selectivity (°C.) |
|---|---|---|---|
| 14 | C | 1.2 | 92.2 |
| 15 | D | 1.3 | 92.1 |
| 16 | E | 1.1 | 87.0 |
| 17 | F | 0.95 | 94.5 |

The results show that within experimental error, catalysts of similar high activity may be generated using a range of sequential impregnation techniques.

EXAMPLE 18

The procedure of Examples 14-17 was repeated using the catalyst prepared according to procedure G Example 1. The productivity was found to be 1.0 kg/kg cat/h, with 92.7% selectivity. Within experimental error, these results are similar to those obtained in Example 14, even though the catalyst of this Example has Pd crystallites (as determined by XRD) of average size 150 Angstrom, whereas that of Example 14 has an average Pd crystallite size of only 30 Angstrom. The results show that no significant losses of activity and selectivity result when catalysts containing small Pd crystallites of <100 Angstrom are employed in contrast to the teaching of EP-A-No. 147219 (Comparison C).

EXAMPLE 19

The catalyst prepared by procedure C was tested in acetic acid hydrogenation at 50 barg and 227° C. The WHSV was 15, and the ratio hydrogen:acetic acid was 9:1 molar. The catalyst was activated at 280° C.

The acetic acid conversion was 40%, with 96% selectivity. This corresponds to a productivity of 6 kg/kgcat/h acetic acid converted. Under similar conditions but with WHSV=3.6, conversion was 74% with 96% selectivity.

EXAMPLES 20-24

The catalysts prepared by procedure H were tested in the hydrogenation of acetic acid. The catalysts were activated at 300° C. The WHSV was ca 1.1 (LHSV=0.35), and the ratio hydrogen to acetic acid was 11:1 molar. Results are collected in Table 4.

TABLE 4

| Example | Catalyst | P/barg | T/°C. | Conversion (%) | Selectivity (%) |
|---|---|---|---|---|---|
| 20 | H1 | 5 | 200 | 46 | 38 |
| 21 | H2 | 5 | 202 | 43 | 53 |
| 22 | H2 | 10 | 194 | 54 | 58.5 |
| 23 | H3 | 10 | 203 | 35.2 | 8.7 |
| 24 | H4 | 5 | 201 | 22.3 | 5.9 |

The results show the beneficial effect of potassium in improving selectivity, and that catalysts H3 and H4 which are not according to the present invention, show very poor performance.

EXAMPLES 25-28

Catalysts prepared by procedures I and J of Example 1 were examined in the hydrogenation of propionic acid. The procedure of Examples 2-7 was repeated, except that only 2 mls of catalyst was employed, LHSV=1, the ratio of propionic acid to hydrogen was 1:10 molar, the pressure was 9 barg, and the catalyst were activated at 280° C. Results are collected in Table 5. In each case, the concentration of aldehyde in the product was greater than the trace amounts encountered in other Examples. Independent selectivities to aldehyde are therefore reported.

TABLE 5

| Example | Catalyst | T/°C. | Conversion (%) | Selectivity (%) | Selectivity (% aldehyde) |
|---|---|---|---|---|---|
| 25 | I | 202 | 22.5 | 97 | 4 |
| 26 | I | 223 | 32.0 | 94 | 3 |
| 27 | J | 201 | 12.5 | 97 | 5 |
| 28 | J | 222 | 23.0 | 96 | 5 |

The results show that sequential impregnation of Ru then Re yields better catalysts then sequential impregnation of Re then Ru.

EXAMPLES 29 AND 30

The catalysts prepared by procedure K Example 1 were tested in the hydrogenation of acetic acid. The procedure of Examples 2-7 was adopted, except that the catalyst of Example 30 was activated at 450° C., and that of 29 at 300° C. Results are collected in Table 6.

TABLE 6

| Example | Catalyst | T/°C. | Conversion (%) | Selectivity (%) |
|---|---|---|---|---|
| 29 | K | 209 | 12.2 | 91.7 |
| 30 | K | 210 | 10.5 | 95.3 |

EXAMPLE 31

The catalyst prepared by procedure L was employed for the hydrogenation of acetic acid, according to the procedure of Examples 14–17. The conversion was 11.0% (productivity 0.5 kg/kg cat/h converted) with 93.8% selectivity.

EXAMPLE 32

The catalyst prepared according to procedure B1 was used for the liquid phase hydrogenation of acetic acid. 1.01 g of the powdered catalyst was charged to a 100 ml stainless steel autoclave, along with 50.2 g of acetic acid. The autoclave was flushed and then pressurised with hydrogen to 100 barg, and heated with stirring to 200° C., at which temperature it was held for 6.0 hours. After cooling, the liquid phase product was removed and filtered, and analysed both for organic products and rhenium and palladium metals. The final pressure after cooling was 50 barg.

The product was found to contain 27.9% wt ethyl acetate and 2% wt ethanol (corresponding to a productivity of 1.5 kg/kg cat/h converted by hydrogenation). In addition, 16% of the rhenium and 0.06% of the palladium originally on the catalyst was found to have leached into solution.

This example demonstrates that considerable leaching of rhenium can occur in the liquid phase hydrogenation of acetic acid. This is in contrast to reactions carried out in the gas phase, where no detectable loss of rhenium occurs.

This is not an example according to the present invention because it was carried out in the liquid phase. It is included only for the purpose of comparison.

We claim:

1. A process for the production of either ethanol from acetic acid or propanol from propionic acid together with the coproduction of the corresponding ester in each case which process comprises contacting either acetic acid or propionic acid in the vapor phase with hydrogen at elevated temperature and pressure in the range from 1 to 150 bar in the presence of a catalyst essentially consisting of (i) a noble metal of Group VIII of the Periodic Table of Elements, and (ii) rhenium, and either (a) increasing the proportion of coproduced corresponding ester by operating at low conversions per pass or by introducing an acidic function component in to the catalyst, or (b) increasing the proportion of alcohol by cofeeding water or by operating at high conversions per pass.

2. A process according to claim 1 wherein the noble metal of Group VIII is palladium.

3. A process according to claim 1 wherein the noble metal of Group VIII is ruthenium.

4. A process according to claim 1 wherein the catalyst is supported.

5. A process according to claim 4 wherein the support is a high surface area graphitised carbon.

6. A process according to claim 4 wherein the support is a silica.

7. A process according to claim 1 wherein the catalyst is modified by incorporation of a metal of Group IA of the Periodic Table of the Elements.

8. A process according to claim 7 wherein the modifying metal is potassium.

9. A process according to claim 1 wherein the catalyst is activated before use by contact at elevated temperature with either hydrogen or a hydrogen/inert gas mixture at a temperature in the range from 200° to 350° C. for a period of from 1 to 20 hours.

10. A process according to claim 1 wherein the catalyst is activated by heating to the reaction temperature in the presence of reactants.

* * * * *